United States Patent
Surti et al.

(10) Patent No.: US 7,282,057 B2
(45) Date of Patent: Oct. 16, 2007

(54) PEDIATRIC ATRESIA MAGNETS

(75) Inventors: Vihar C. Surti, Winston-Salem, NC (US); Mario Zaritzky, La Plata (AR)

(73) Assignee: Wilson-Cook Medical, Inc., Winston-Salem, NC (US)

( * ) Notice: Subject to any disclaimer, the term of this patent is extended or adjusted under 35 U.S.C. 154(b) by 205 days.

(21) Appl. No.: 10/802,555

(22) Filed: Mar. 30, 2004

(65) Prior Publication Data
US 2005/0228412 A1 Oct. 13, 2005

(51) Int. Cl.
*A61B 17/08* (2006.01)

(52) U.S. Cl. .................. 606/153; 604/264

(58) Field of Classification Search .......... 604/264, 604/508–10, 529, 102.2–102.3, 103.01–103.4; 600/101, 115, 123, 156, 593; 606/41, 153, 606/185; 128/898; 607/122
See application file for complete search history.

(56) References Cited

U.S. PATENT DOCUMENTS

| | | | | |
|---|---|---|---|---|
| 2,308,484 A | * | 1/1943 | Auzin et al. | 156/245 |
| 3,771,526 A | * | 11/1973 | Rudie | 606/153 |
| 3,986,493 A | * | 10/1976 | Hendren, III | 600/12 |
| 4,294,362 A | * | 10/1981 | Martensson | 229/216 |
| 4,619,247 A | | 10/1986 | Inoue et al. | |
| 4,873,977 A | | 10/1989 | Avant et al. | |
| 4,978,323 A | | 12/1990 | Freedman | |
| 5,429,131 A | | 7/1995 | Scheinman et al. | |
| 5,681,260 A | | 10/1997 | Ueda et al. | |
| 5,690,656 A | | 11/1997 | Cope et al. | |
| 6,352,543 B1 | | 3/2002 | Cole | |
| 6,985,776 B2 | * | 1/2006 | Kane et al. | 607/122 |
| 2003/0130610 A1 | * | 7/2003 | Mager et al. | 604/6.16 |
| 2003/0139703 A1 | * | 7/2003 | Burkett et al. | 604/96.01 |
| 2004/0034377 A1 | | 2/2004 | Sharkawy et al. | |

* cited by examiner

*Primary Examiner*—Nicholas D. Lucchesi
*Assistant Examiner*—Christopher D. Koharski
(74) *Attorney, Agent, or Firm*—Brinks Hofer Gilson & Lione

(57) ABSTRACT

A medical system for approximating the esophageal sacs in an infant afflicted with esophageal atresia. The medical device includes an esophageal catheter and a gastric catheter. The distal end of the esophageal catheter, which includes a magnetic tip, is passed through the esophagus to the upper esophageal sac. The distal end of the gastric catheter, which also includes a magnetic tip, is passed through a gastrostomy and into the lower esophageal sac. The magnetic forces created by both magnets results in approximation of the esophageal sacs. Pressure-induced necrosis establishes a passageway between the esophageal sacs. A stent or stent-graft can be deployed within the established passageway to prevent re-synopsis of the esophagus.

13 Claims, 3 Drawing Sheets

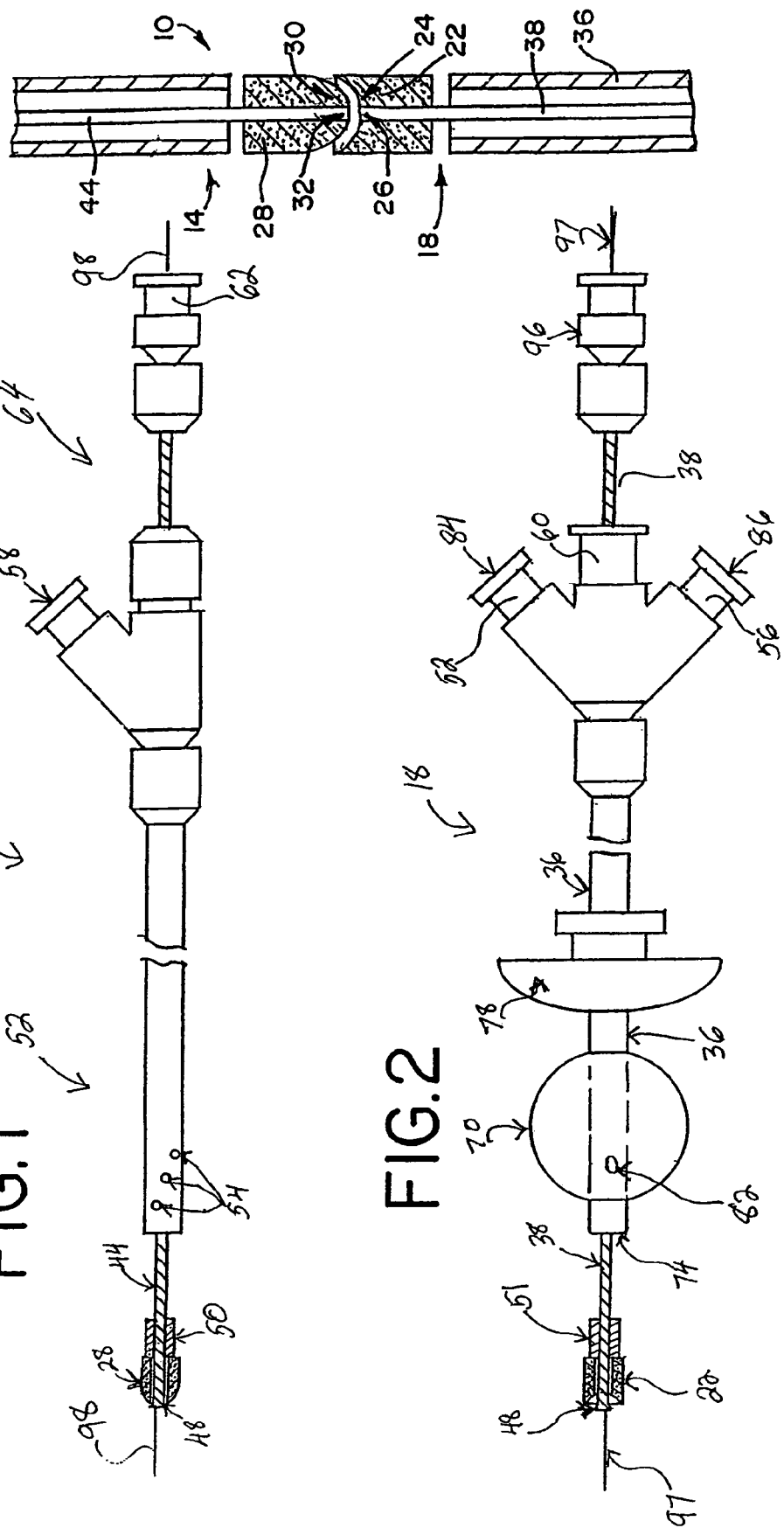

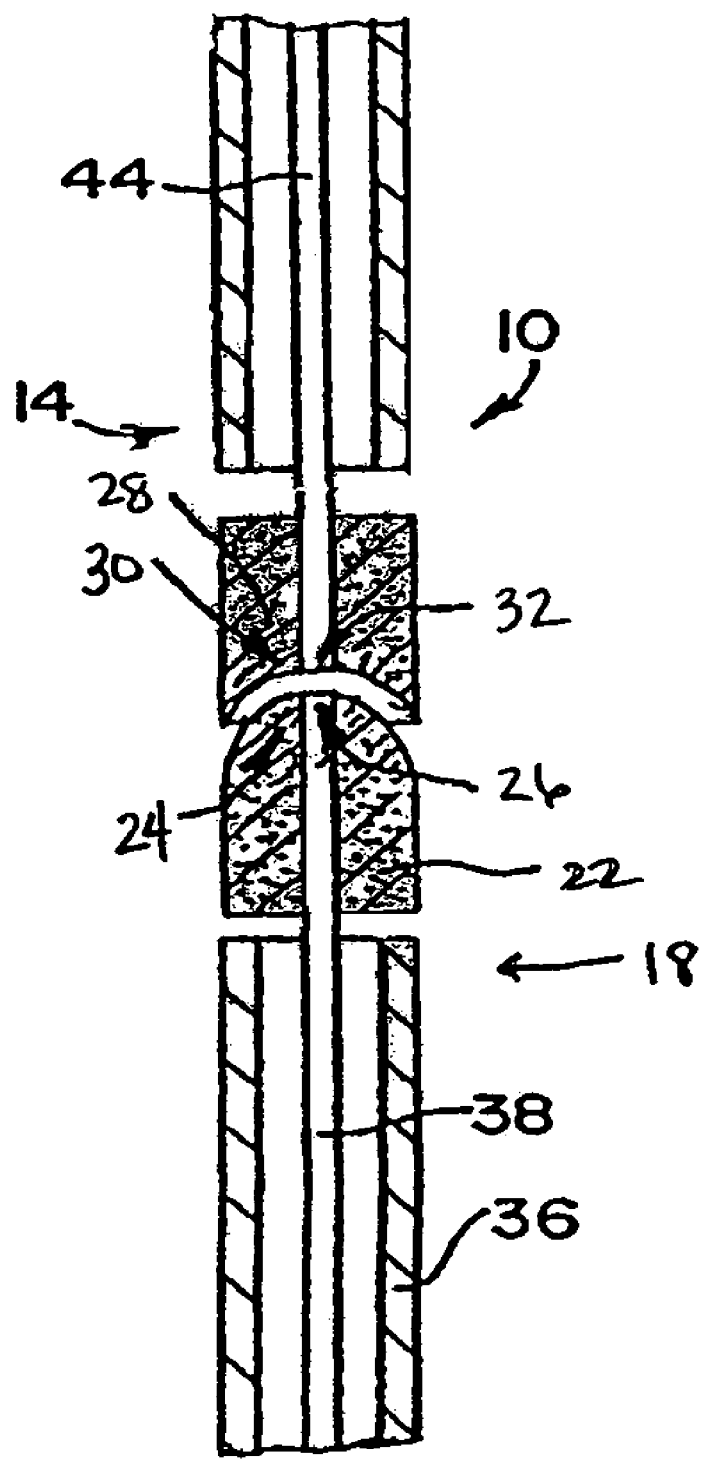

PEDIATRIC ATRESIA MAGNETS

TECHNICAL FIELD

This invention relates to medical devices, and more particularly, to a method and device for non-surgically treating pediatric esophageal atresia.

BACKGROUND

Esophageal atresia is a serious birth defect in which the esophagus, the long tube connecting the mouth to the stomach, is segmented and does not form a continuous passageway into the stomach. In particular, infants suffering from esophageal atresia are born with separate upper and lower esophageal portions (commonly referred to as esophageal sacs). In most forms of esophageal atresia the upper esophageal sac begins to fill with mucus and saliva shortly after birth. Consequently, excessive drooling, choking, and coughing are symptomatic of esophageal atresia. Moreover, an infant afflicted with this disorder instantaneously returns (i.e., expels) what he or she is fed, thereby preventing the digestion and absorption of orally administered foods.

There are several types of esophageal atresia. In one type, the upper and lower esophageal sacs are not attached to the trachea. That is, the lower esophageal sac does not develop an esophagotracheal fistula. In another type, the upper esophageal portion ends as a blind sac, whereas the lower esophageal portion is connected to the trachea by a narrow canal at a point just above the tracheal bifurcation. In yet another type, the narrow canal between the trachea and the distal portion of the esophagus forms a ligamentous cord. In rare instances, both the proximal and distal portions of the esophagus actually open into the trachea.

For a period of about three months after birth, the esophageal sacs spontaneously undergo a period of rapid growth toward each other. A number of different techniques have been used during this spontaneous growth period to achieve a more rapid approximation of the esophageal sacs. These techniques have included, for example, the use of large external electromagnet or surgical techniques.

One such technique is described in detail in U.S. Pat. No. 3,986,493 (hereinafter "the '493 patent"), titled "Electromagnetic Bougienage Method." The '493 patent generally describes a method of preparing an infant for a subsequent primary anastomosis without tension. In particular, the '493 patent describes the use of an external annular electromagnet to intermittently magnetize bougies located within each esophageal sac. Over a period of time, the intermittent force created between the bougies causes the lengthening of the atretic segments. Once the atretic segments are sufficiently lengthened to allow a primary anastomosis, the magnetic bougies are removed and the esophagus is surgically joined.

Yet another method of treating esophageal atresia involves surgically applying sutures to the opposing ends of the esophageal sacs. The sutures create traction forces to the ends of the esophageal sacs during the rapid growth period, thereby causing further elongation of the esophageal sacs. Ultimately, the sutures cause the esophageal sacs to grow together.

The above-described conventional methods of correcting esophageal atresia present several drawbacks. The use of an external electromagnet requires that the infant be placed in a specially constructed bed having a large annular electromagnet. In addition to the expense associated with providing such a bed, the electromagnet itself can significantly impact the ability of caregivers to nurture the infant. In addition, the use of an external electromagnet requires a subsequent procedure to surgically join the esophageal sacs into a continuous lumen. Surgically joining the esophageal sacs requires great surgical skill, and can present significant operative and post-operative complications. For example, surgical joining can result in the misalignment of the esophagus, and consequently, difficulty swallowing. Additional complications include gastroesophageal reflux, which can lead to ulcers in the lower part of the esophagus.

Applying traction through surgically placed sutures also presents several drawbacks. The main drawback of using sutures is the need for a significant surgical procedure once the esophageal sacs are sufficiently lengthened by the traction. This procedure involves surgically joining the esophageal sacs, which can result in a number of the complications detailed above. Moreover, as the sutures draw the esophageal sacs together, the sutures frequently tear out of one or both of the sacs. This requires at least one, and often multiple additional surgeries to re-suture the esophageal sacs.

BRIEF SUMMARY

Accordingly, it is an object of the present invention to provide a medical system and procedure having features that resolve or improve upon one or more of the above-described procedures and avoids the drawbacks associated therewith.

The foregoing object is obtained by providing a medical system for joining an upper esophageal sac and a lower esophageal sac. According to a first aspect of the present invention, a novel medical system and procedure is provided for non-surgically correcting esophageal atresia. The medical system includes first and second catheters. Each catheter is configured to deliver a magnet to the terminal end of the esophageal sacs. Once in place, the magnets are configured to align the esophageal sacs and provide a constant traction force and subsequently establish a passageway from the mouth to the stomach of the infant.

The first catheter is adapted for insertion through the mouth and into the first esophageal sac. The catheter includes a proximal end, a distal end, and one or more passageways disposed longitudinally therebetween. One such passageway can be adapted to provide suction for removing any fluids, such as saliva and/or mucous. Also, a catheter carrying a magnet at its distal end can be slidably disposed through one passageway so as to create a constant magnetic force at the distal end of the first elongate member.

The second catheter is inserted through a gastrostomy and into the second esophageal sac. The second catheter includes a proximal end, a distal end, and several passageways disposed therebetween. The passageways serve several functions. One passageway is adapted to slidably receive a catheter that carries a magnet. A second passageway is adapted for inflating and deflating a balloon, which is operatively connected to a distal portion of the second catheter. In use, the balloon is positioned inside the infant's stomach and prevents the second elongate member from accidentally dislodging from the gastrostomy. A third passageway is adapted for feeding milk and/or other nutrients, medications, etc., directly into the infant's stomach.

Once the first and second catheters are placed within the esophageal sacs, the attractive force between both magnets naturally draws the magnets together, thereby exerting a constant traction force on each esophageal sac to promote rapid growth thereof. Once the esophageal sacs are in contact with each other, the magnets cause the sacs to grow together and form an anastomosis therethrough. The magnets can be formed into a variety of shapes to facilitate alignment, coupling or mating therebetween. For example, one magnet can be bullet-shaped and the other magnet can be configured to receive the bullet-shaped magnet.

BRIEF DESCRIPTION OF THE DRAWINGS

FIG. 1 is a side view of the esophageal catheter of the present invention that is introduced into the upper esophageal sac through the mouth.

FIG. 2 is a side view of the gastric catheter of one embodiment of the present invention.

FIG. 3 is a sectional side view of the esophageal catheter and the gastric catheter with reference to exemplary magnetic tips at the distal ends of both catheters.

FIG. 6 is a sectional side view of an alternative embodiment of the magnetic tips shown in FIG. 3.

DETAILED DESCRIPTION OF THE INVENTION

Figure 4:
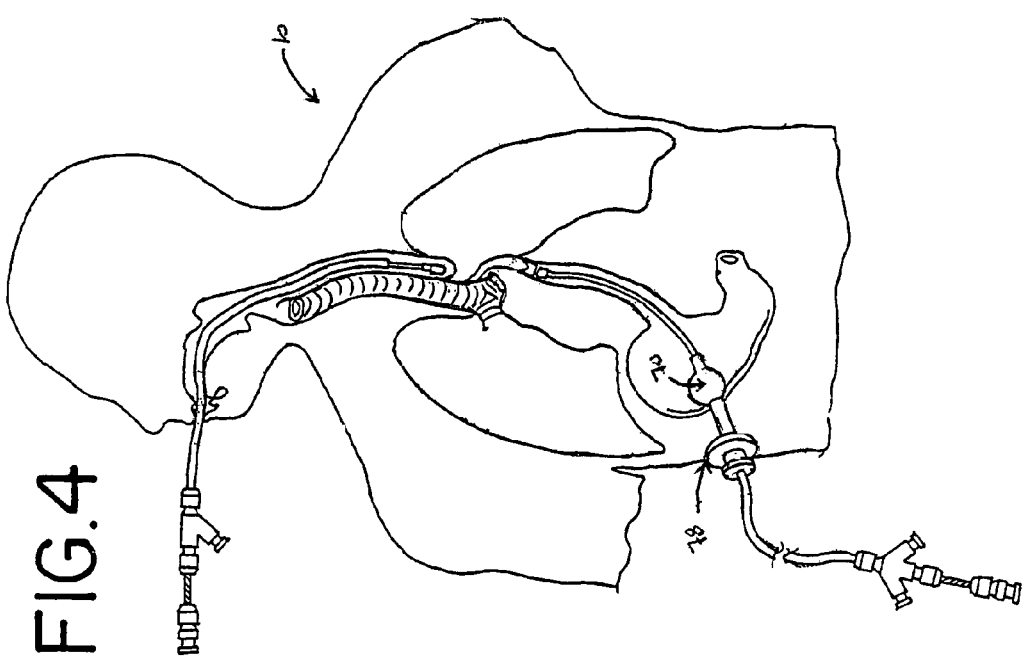
FIG. 4 is a view of one embodiment of the present invention located within an infant.

The invention is described with reference to the drawings in which like elements are referred to by like numerals. The relationship and functioning of the various elements of this invention are better understood by the following detailed description. However, the embodiments of this invention as described below are by way of example only, and the invention is not limited to the embodiments illustrated in the drawings. It should also be understood that the drawings are not to scale and in certain instances details have been omitted, which are not necessary for an understanding of the present invention, such as conventional details of fabrication and assembly. Additionally, it should be noted that, as used herein, the term "magnet" refers to a material that is naturally surrounded by a magnetic field and has the property of attracting iron or steel.

Referring to the drawings, FIGS. 1-5 depict an illustrative embodiment of the present invention. Generally, a medical system 10 is provided to correct esophageal atresia in an infant. As best illustrated in FIGS. 1 and 2, medical device 10 includes esophageal catheter 14 and gastric catheter 18. The esophageal catheter is configured to pass a first magnet through the esophagus and into abutment with the terminus of the upper esophageal sac. In addition, the esophageal catheter is provided with a plurality of ports for removing fluids that collect within the upper esophageal sac. The gastric catheter, on the other hand, is configured to pass a second magnet through the stomach and into the terminus of the lower esophageal sac. When in place, both magnets are approximated by their magnetic force, thereby imparting a constant traction upon the esophageal sacs. Additionally, both magnets are configured so that the approximating force therebetween properly aligns the esophageal sacs.

Referring to FIG. 1, esophageal catheter 14 generally comprises an elongate, tubular sheath having a distal end 52 and a proximal end 64. The esophageal catheter shaft is preferably formed of a biocompatible polymer having a smooth outer surface and a radius of approximately 10 french, so as to allow relatively effortless passage into the esophagus of an infant. One preferred material for the esophageal catheter is high density polyethelene.

Esophageal catheter 14 includes at least two lumens extending longitudinally therethrough. The first lumen extends from ports 54, which are located at distal end 52, to proximal port 58. In use, suction can be applied to proximal port 58 to remove any fluid or mucous that collects within the upper esophageal sac. The second lumen is sized to slidably accept a catheter 44. One example of a suitable catheter is the Polyetheretherketone Catheter (Wilson-Cook Medical). Catheter 44 is provided with a flared distal tip 48 and a lumen sized to accept a standard wire guide 98, such as a 0.025" METRO™ Wire Guide (Wilson-Cook Medical).

As illustrated in FIG. 1, magnet 28 is fixed to a distal portion of catheter 44. Magnet 28 is fixed to catheter 44 between flared distal tip 48 and metal band 50.

Figure 5:
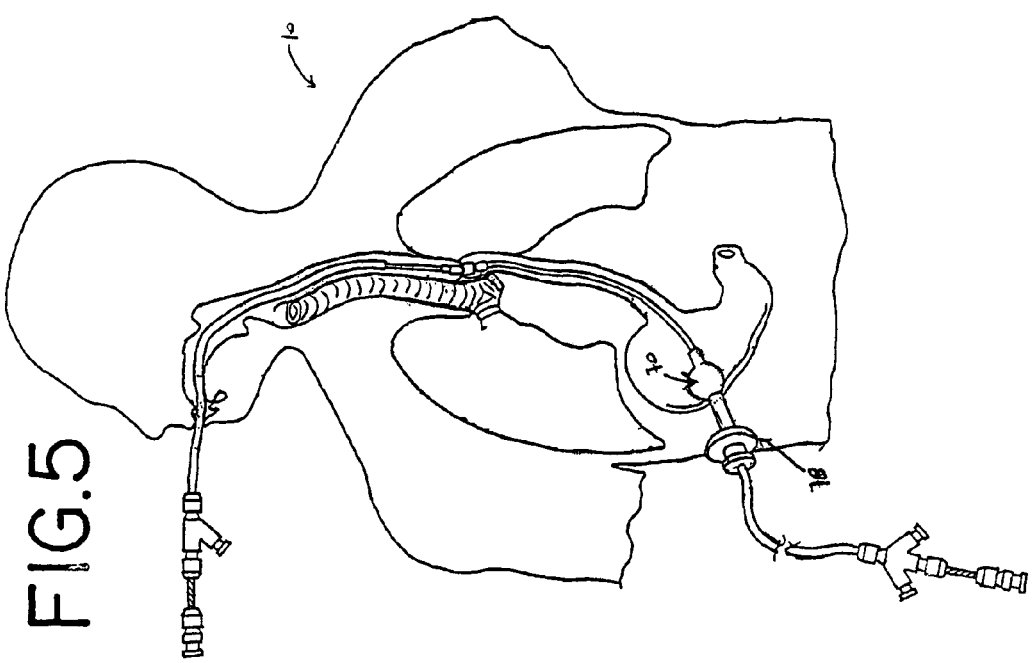
FIG. 5 is a view of one embodiment of the present invention after an anastomosis has formed between two exemplary magnetic tips.

FIG. 2 depicts an illustrative embodiment of the gastric catheter of the present invention. In particular, FIG. 2 illustrates a gastric catheter 18. Gastric catheter 18 includes at least first, second, and third lumens that are accessible via hub connectors 52, 56, 60, respectively. The first lumen is adapted to inflate balloon 70. Specifically, the first lumen extends between inflation port 82, which is located inside balloon 70, and inflation port 84. As best shown in FIGS. 4 and 5, balloon 70 is used in conjunction with bolus 78 to secure fit the gastric catheter to the stomach wall and to prevent any leaking of gastric contents outside of the stomach.

Turning now to FIG. 2, gastric catheter 18 further includes a second lumen. The second lumen is sized to slidably accept a catheter 38. One example of a suitable catheter is the Polyetheretherketone Catheter (Wilson-Cook Medical). Catheter 38 is similar to catheter 44 in that it includes a flared distal tip 48 and a lumen sized to accept a standard wire guide 97, such as a 0.025" METRO™ Wire Guide (Wilson-Cook Medical). Notably, catheter 38 is at least long enough that a distal portion of catheter 38 can reach the terminus of the lower esophageal sac.

In the illustrative embodiment of gastric catheter 18, magnet 22 is fixed to a distal portion of catheter 38 so as to prevent separation of magnet 22 from catheter 38. Magnet 22 can be fixed to catheter 38 in essentially the same manner as magnet 28 is fixed to catheter 44. That is, as illustrated in FIG. 2, magnet 22 is glued to the catheter and additionally secured between flared distal tip 48 and band 51.

It should be noted that both magnets 22 and 28 can be provided in a variety of shapes. For example, the magnet 28 may include bullet-shaped end 30 and the magnet 22 may include a bullet-shaped recess 24 or alternatively, the magnet 22 may include bullet-shaped end 30 and the magnet 28 may include a bullet-shaped recess 24 as shown in FIGS. 3 and 6, respectively. The magnet 22 may include a passageway 26 therethough and the magnet 28 may include a passageway 32 therethough. As also shown in FIGS. 3 and 6, the magnets 22 and 28 can be shaped so as to nest and/or create a continuous passageway between catheter 44 and catheter 38. This continuous passageway allows the insertion of a guide wire from proximal hub assembly 96 through both the gastric catheter and the esophageal catheter, and through port 62 of the esophageal catheter. As a result, once communication is established between both catheters (as detailed below), a wire guide can be used to secure the esophageal lumen between the stomach and the mouth of the infant.

Referring to FIG. 2, gastric catheter 18 also includes a feeding tube 36, which is adapted to pass through a gastrostomy (FIGS. 4 and 5). Feeding tube 36 is adapted to deliver nutrients from port 86 to an infant's stomach via distal port 74. Additionally, if necessary, medications or other fluids can also be delivered to the infant's stomach through feeding tube 36.

FIG. 4 depicts the illustrative esophageal and gastric catheters being used to approximate the upper and lower esophageal sacs of an infant. First, a gastrostomy is performed on the infant and gastric catheter 18 is inserted into the infant's stomach. This procedure is performed using standard fluoroscopic techniques. The gastric catheter should be inserted until bolus 78 abuts the infant's abdomen. At this point in the procedure, a contrast fluid (e.g., Barrium) is injected through port 84 and into balloon 70. This causes balloon 70 to expand, thereby securing catheter 18 to the stomach wall, as illustrated in FIG. 4. After gastric catheter 18 is in place and secured, catheter 38 is advanced distally through the stomach, beyond the lower esophageal sphincter, and into the lower esophageal sac. When properly in place, magnet 22 abuts the terminus of the lower esophageal sac.

Once magnet 22 is situated adjacent the terminus of the lower esophageal sac, esophageal catheter 14 can be inserted. As illustrated in FIG. 4, the esophageal catheter is advanced into the mouth of the infant and distally down the lumen of the upper esophageal sac. Alternatively, the esophageal catheter can be advanced through the infant's nasal passage. In either case, magnet 28 is advanced until it abuts the terminus of the upper esophageal sac. At this point, magnet 28 can be attracted by magnet 22, thereby providing traction forces and aligning the esophageal sacs.

Over a period of about 5 to 7 days the traction caused by magnets 28 and 22 will cause the esophageal sacs to approximate and subsequently physically join together so as to form a continuous esophageal passageway. The constant magnetic force created by the magnets initially causes the esophageal sacs to rapidly grow together and causes pressure-induced necrosis of the esophageal sacs. The continuation of the pressure-induced necrosis along with the rapid growth ultimately results in the formation of a continuous lumen from the mouth to the stomach. As noted above, the magnets are configured to align and connect with each other so as to create a continuous passageway between catheter 44 and catheter 38.

At this point in the procedure, a single guide wire is delivered through the continuous passageway formed by catheters 44 and 38. Thereafter, the esophageal and gastric catheters can be removed from the infant. A feeding tube is then placed over the guide wire and the guide wire is removed.

After the procedure is complete, the infant should be periodically observed for any signs of re-synopsis. If any re-synopsis is observed, a balloon catheter can be used to perform an esophageal dilation. In addition to esophageal dilation, a stent or stent-graft can be placed within the esophagus in the area of the synopsis. Alternatively, a stent or stent graft can be used to prevent any such re-synopsis.

Any other undisclosed or incidental details of the construction or composition of the various elements of the disclosed embodiment of the present invention are not believed to be critical to the achievement of the advantages of the present invention, so long as the elements possess the attributes needed for them to perform as disclosed. Certainly, one skilled in the medical arts would be able to conceive of a wide variety of magnet shapes and sizes successful combinations thereof. The selection of these and other details of construction are believed to be well within the ability of one of even rudimental skills in this area, in view of the present disclosure. Illustrative embodiments of the present invention have been described in considerable detail for the purpose of disclosing a practical, operative structure whereby the invention may be practiced advantageously. The designs described herein are intended to be exemplary only. The novel characteristics of the invention may be incorporated in other structural forms without departing from the spirit and scope of the invention. The invention encompasses embodiments both comprising and consisting of the elements described with reference to the illustrative embodiments. Unless otherwise indicated, all ordinary words and terms used herein shall take their customary meaning as defined in *The American Heritage Dictionary*, Third Edition. All technical terms shall take on their customary meaning as established by the appropriate technical discipline utilized by those normally skilled in that particular art area. All medical terms shall take their meaning as defined by *Stedman's Medical Dictionary*, 27th edition.

What is claimed is:

1. A medical system for joining an upper esophageal sac and a lower esophageal sac in an infant, the medical device comprising:
    a first elongate member comprising an operative end, a distal end and an upper magnet having a constant magnetic force connected to the distal end, the upper magnet comprising an end portion having one of a protruding surface or a recessed surface and the upper magnet further having an upper magnet passageway therethrough and being configured to abut an interior surface of the upper esophageal sac; and
    a second elongate member comprising an operative end, a distal end, and a lower magnet connected to the distal end, the lower magnet comprising an end portion having the other of a protruding surface or a recessed surface and the lower magnet further having a lower magnet passageway and being configured to abut an interior surface of the lower esophageal sac;
    wherein the upper magnet and the lower magnet are configured to mate so as to approximate the upper esophageal sac and the lower esophageal sac, and further wherein the upper and lower magnet passageways operably connect to form a substantially continuous passageway between the upper magnet and the lower magnet when the upper and lower esophageal sacs are joined.

2. The medical system of claim 1, wherein the upper magnet is bullet-shaped and the lower magnet comprises a bullet-shaped recess.

3. The medical system of claim 1, wherein the upper magnet comprises a bullet-shaped recess and the lower magnet is bullet-shaped.

4. The medical system of claim 1, further comprising: a guide wire; and
    a passageway extending axially through the first elongate member, the passageway being adapted to receive the guide wire.

5. The medical system of claim 1, wherein the first elongate member further comprises:
    a passageway extending axially through the first elongate member; and
    a flexible elongate member extending axially through the interior of the passageway, the flexible elongate member being operatively connected to the upper magnet.

6. The medical system of claim 1, wherein the second elongate member further comprises:
    a passageway extending axially through the second elongate member; and a flexible elongate member extending axially through the passageway, the flexible elongate member being operatively connected to the lower magnet.

7. The medical system of claim 6, wherein the second elongate member further comprises:
a balloon; and
a second passageway extending axially through the second elongate member, the second passageway having a distal end and an operative end, the distal end of the second passageway being connected to the balloon; and
a balloon operation hub operatively connected to the operative end of the second passageway.

8. The medical device of claim 7, wherein the second elongate member further comprises:
a plurality of ports;
a third passageway extending axially through the second elongate member, the third passageway having a distal end and an operative end, the distal end of the third passageway being configured to communicate with the plurality of ports; and
a gastrostomy hub operatively connected to the operative end of the third passageway.

9. The medical system of claim 6, further comprising a hub operatively connected to the operative end of the second elongate member; and a valve operatively connected to the hub.

10. The medical system of claim 1, wherein the second elongate member further comprises:
a balloon; and
a passageway extending axially through the elongate member, the passageway having a distal end and an operative end, the distal end of the passageway being connected to the balloon; and
a balloon operation hub operatively connected to the operative end of the passageway.

11. The medical device of claim 1, wherein the second elongate member further comprises:
a plurality of ports;
a passageway extending axially through the second elongate member, the passageway having a distal end and an operative end, the distal end of the passageway being configured to communicate with the plurality of ports; and
a gastrostomy hub operatively connected to the operative end of the passageway.

12. The medical system of claim 1, further comprising a band and a flared distal portion, wherein the upper magnet is secured to the distal end of the first elongate member by the band and the flared distal portion.

13. A medical system for joining an upper esophageal sac and a lower esophageal sac, the medical system comprising:
an esophageal catheter comprising:
an operative end, a distal end, and an upper magnet, the upper magnet having a constant magnetic force and being configured to abut an interior surface of the upper esophageal sac; and
a passageway extending axially through the esophageal catheter; and
a gastric catheter comprising:
an operative end, a distal end, and a lower magnet, the lower magnet being configured to abut an interior surface of the lower esophageal sac, wherein the upper magnet is configured to constantly attract the lower magnet;
a passageway extending axially through the gastric catheter, the passageway having an operative end;
a hub operatively connected to the operative end of the passageway; a balloon; a second passageway extending axially through the gastric catheter, the second passageway having a distal end and an operative end, the distal end of the passageway being connected to the balloon;
a balloon operation hub operatively connected to the operative end of the second passageway; a plurality of ports;
a third passageway extending axially through the gastric catheter, the third passageway having a distal end and an operative end, the distal end of the third passageway being configured to communicate with the plurality of ports; and
a hub operatively connected to the operative end of the third passageway,
wherein the upper and lower magnets are configured to mate so that the esophageal catheter passageway is operably connectable to the gastric catheter passageway to create a substantially continuous passageway therethrough when the upper and lower esophageal sacs are joined.

* * * * *